(12) United States Patent
Adler

(10) Patent No.: US 7,101,507 B1
(45) Date of Patent: Sep. 5, 2006

(54) SLURRY TREATMENT AND SHIPPING METHOD

(76) Inventor: Paul E. Adler, 103 Georgetown Ct., Macon, GA (US) 31210

( * ) Notice: Subject to any disclaimer, the term of this patent is extended or adjusted under 35 U.S.C. 154(b) by 0 days.

(21) Appl. No.: 09/701,455
(22) PCT Filed: May 27, 1999
(86) PCT No.: PCT/US99/11709
§ 371 (c)(1), (2), (4) Date: Feb. 5, 2001
(87) PCT Pub. No.: WO99/61074
PCT Pub. Date: Dec. 2, 1999

Related U.S. Application Data
(60) Provisional application No. 60/087,375, filed on May 28, 1998.

(51) Int. Cl.
A61L 2/04 (2006.01)
(52) U.S. Cl. .............. 422/1; 422/308; 165/66
(58) Field of Classification Search .............. 422/32, 422/38, 307, 308, 309, 1, 41; 241/23, 46.01, 241/65, 606; 165/66
See application file for complete search history.

(56) References Cited

U.S. PATENT DOCUMENTS

| | | | |
|---|---|---|---|
| 3,612,278 A | * | 10/1971 | Dieterich ................ 210/177 |
| 3,871,824 A | | 3/1975 | Rechtsteiner et al. .......... 21/58 |
| 5,225,221 A | | 7/1993 | Camden et al. ............... 426/74 |
| 5,397,754 A | | 3/1995 | Iannicelli et al. ........... 501/146 |
| 5,496,398 A | | 3/1996 | Drew et al. ............. 106/15.05 |
| 5,498,396 A | | 3/1996 | Aikus et al. ................ 422/109 |
| 5,603,894 A | * | 2/1997 | Aikus et al. ................. 422/23 |
| 5,759,491 A | | 6/1998 | Bunin ........................ 422/38 |
| 5,788,858 A | * | 8/1998 | Acernese et al. ........ 210/257.2 |
| 5,817,253 A | * | 10/1998 | Grimberg et al. ...... 252/186.29 |
| 5,888,453 A | | 3/1999 | Luker .......................... 422/38 |

* cited by examiner

Primary Examiner—E. Leigh McKane
(74) Attorney, Agent, or Firm—David A. Greenlee

(57) ABSTRACT

Aerobic and anaerobic contamination is removed from a slurry by a sterilizing process and apparatus (10). A slurry piping circuit (26, 28, 30, 32, 34) interconnects a supply tank (12), three serial heat exchangers (16, 18, 20) and a storage tank (14). The circuit and storage tank are sanitized by flushing with mist of hydrogen peroxide (44) and nitrogen (50). One heat exchanger (16) transfers heat from the sterilized slurry to the unsterilized slurry. A closed hot water piping circuit (60, 62, 64) interconnects a hot water boiler (22) and the other two heat exchangers (18, 20). The slurry is sterilized in an insulated manifold (24) interconnecting the other two heat exchangers (18, 20). Slurry is pumped through the piping and heated by hot water in the manifold to kill the bacteria, and is covered by a layer of nitrogen (54) in the storage tank (14). The storage tank may be transported to a distant terminus where it is unloaded and again sterilized, if necessary, or is used immediately in an industrial process.

17 Claims, 3 Drawing Sheets

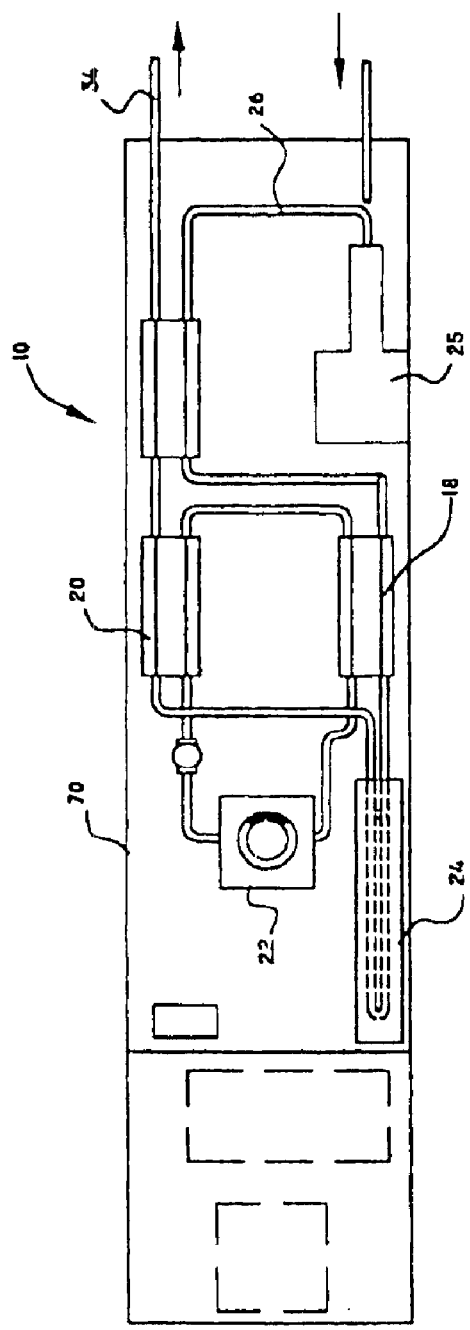
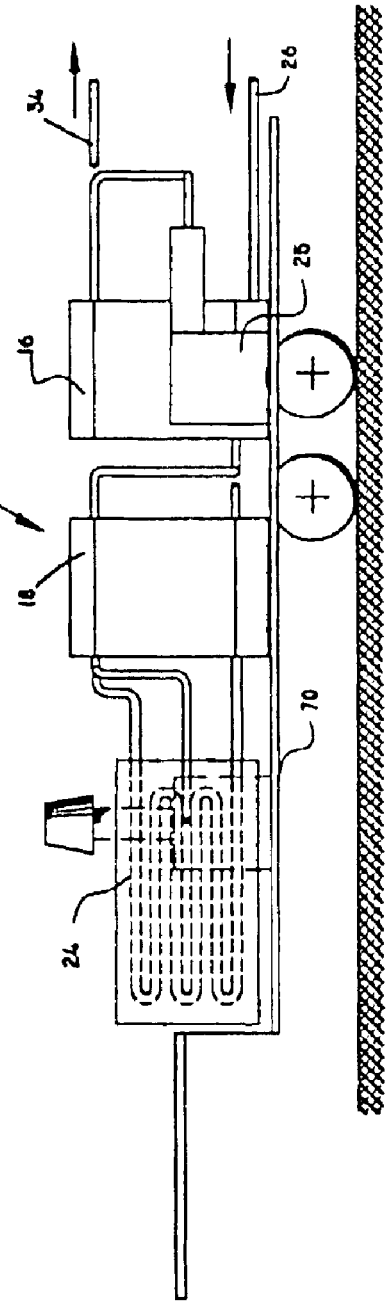
FIG. 3
FIG. 4

SLURRY TREATMENT AND SHIPPING METHOD

This application claims benefit of Ser. No. 60/087,375 filed May 28, 1998.

TECHNICAL FIELD

This invention relates generally to treating contaminatable slurries and, more particularly, to a process and apparatus for sterilizing and a method of shipping these slurries.

BACKGROUND OF THE INVENTION

Many processes exist for treating mined kaolin during the beneficiation process to improve the physical and chemical aspects of the resulting slurry, or slip, to improve its commercial value. Many of these remove contaminants of various types to improve the whiteness and purity of the kaolin and additionally employ the use of oxidation, leaching and magnetic separation. Such processes are detailed in U.S. Pat. No. 5,397,754.

Slurries of beneficiated kaolin calcium carbonate, titanium dioxide, talc, latex, other carbonates and mixtures thereof are used extensively in the paper, paint, rubber and plastics industries as coatings, fillers, extenders and pigments. These slurries are contaminatable (i.e. subject to contamination) by aerobic and anaerobic bacteria. Such contamination affects the color, odor and viscosity of the slurries, which negatively affect their commercial value.

Many treatments to neutralize the effects of this bacteria on kaolin slurries have been tried. The most conventional treatment is mixing a bactericide into the slurry to kill the bacteria. An example of this treatment is found in U.S. Pat. No. 5,496,398. Unfortunately, this treatment has a very limited period of effectiveness until contamination again occurs, because the bacteria are not completely destroyed and exposure to air produces recontamination by the aerobic bacteria that thrive on the available oxygen. Thus, the slurry must be re-treated if it is not quickly used. This repeated use of such chemicals increases the cost of producing and maintaining these slurries at acceptable levels of bacteriological contamination while assuring that the performance properties of the slurries are not degraded.

The limited life of such a treatment process presents a problem when contaminatable slurries are stored for long periods of time, a problem that is exacerbated by the conventional practice of storing slurries in open top tanks. Often, the treated slurries are shipped for long distances by truck, rail or ship, which produce re-contamination for the same reasons.

There is a need for a method of treating and shipping kaolin and calcium carbonate and other contaminatable slurries which eliminates bacterial contamination during storage and shipping and eliminates the necessity for repeated treatment by bactericides.

SUMMARY OF THE INVENTION

It is therefore an object of this invention to provide for a method of treating and shipping kaolin and calcium carbonate and other contaminatable slurries which eliminates bacterial contamination during storage and shipping and eliminates the necessity for repeated treatment by bactericides.

According to a preferred embodiment of this invention, apparatus is provided for sterilizing slurries subject to aerobic and anaerobic contamination. A slurry piping circuit interconnects a supply tank, three serial heat exchangers, and a storage tank. The circuit and storage tank are sanitized by flushing with hydrogen peroxide. One heat exchanger transfers heat from the sterilized slurry to the unsterilized slurry. A closed hot water piping circuit interconnects a hot water boiler and the other two heat exchangers. The piping interconnecting the other two heat exchangers is an insulated manifold where the slurry is sterilized. Slurry is pumped through the piping and heated by hot water in the manifold to kill the bacteria, and is stored and covered by a layer of nitrogen. It may be transported to a distant terminus where it is unloaded and again sterilized, if necessary, or be stored locally, or be used immediately in an industrial process.

In one aspect, this invention features a process for sterilizing contaminatable slurries, which comprises the steps of providing a sanitized fluid handling system, pumping the slurry through the system at a predetermined flow rate, heating the slurry to a sterilizing temperature of about 210° F.–290° for a predetermined time to sterilize the slurry, cooling the slurry to a temperature below 100° F., and transferring the sterilized slurry to a sanitized, oxygen-free fluid collection device, which may be a stationary or transportable storage tank or the supply system for a further industrial process.

In another aspect of this invention, the process includes the further steps of excluding oxygen from the tank by covering the sterilized slurry with a blanket of nitrogen, and transporting the storage tank to a terminus for offloading of the slurry and re-sterilizing if necessary.

In yet another aspect, this invention features fluid handling and sterilizing apparatus for sterilizing contaminatable slurries, which includes a supply tank for holding unsterilized slurry, and a sterilizing unit for heating slurry to a sterilizing temperature. A heat exchanger transfers heat from the sterilized slurry to the unsterilized slurry, thus preheating the unsterilized slurry and cooling the sterilized slurry. A slurry piping circuit connects the supply tank to the heat exchanger and connects the heat exchanger to the sterilizing unit for handling the unsterilized slurry, and connects the sterilizing unit to the heat exchanger and exits the heat exchanger for handling the sterilized slurry. A pump pumps slurry through the piping circuit at a predetermined pressure in order to maintain all slurry in a liquid state, regardless of temperature.

In a further aspect of this invention, the sterilizing unit includes a heating unit, a second heat exchanger for transferring heat from the heating unit to the unsterilized slurry to raise the temperature of the unsterilized slurry to a sterilizing temperature, a manifold for maintaining the heated slurry at the sterilizing temperature, and a third heat exchanger for transferring heat from the sterilized slurry to the heating unit to cool the sterilized slurry.

These and further objects and features of this invention will become readily apparent from a review of the following detailed description of a preferred embodiment, as illustrated in the accompanying drawings, in which:

BRIEF DESCRIPTION OF THE DRAWINGS

FIGS. 3 and 4 are plan and side views of the system of FIG. 1, shown mounted on a semi-trailer.

DESCRIPTION OF THE PREFERRED EMBODIMENT

Figure 1:
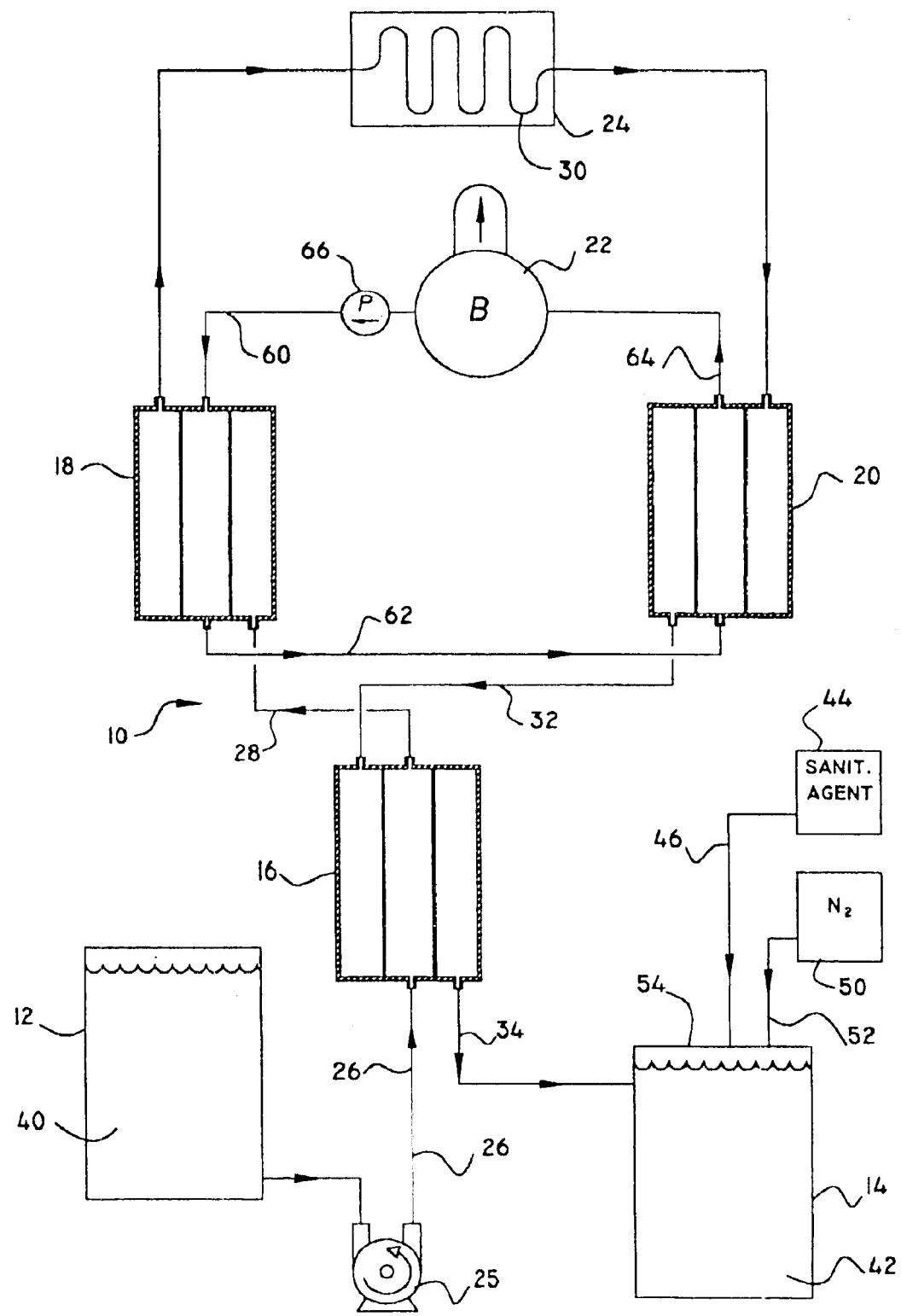
FIG. 1 is a schematic representation of the apparatus and process according to this invention.
Figure 2:
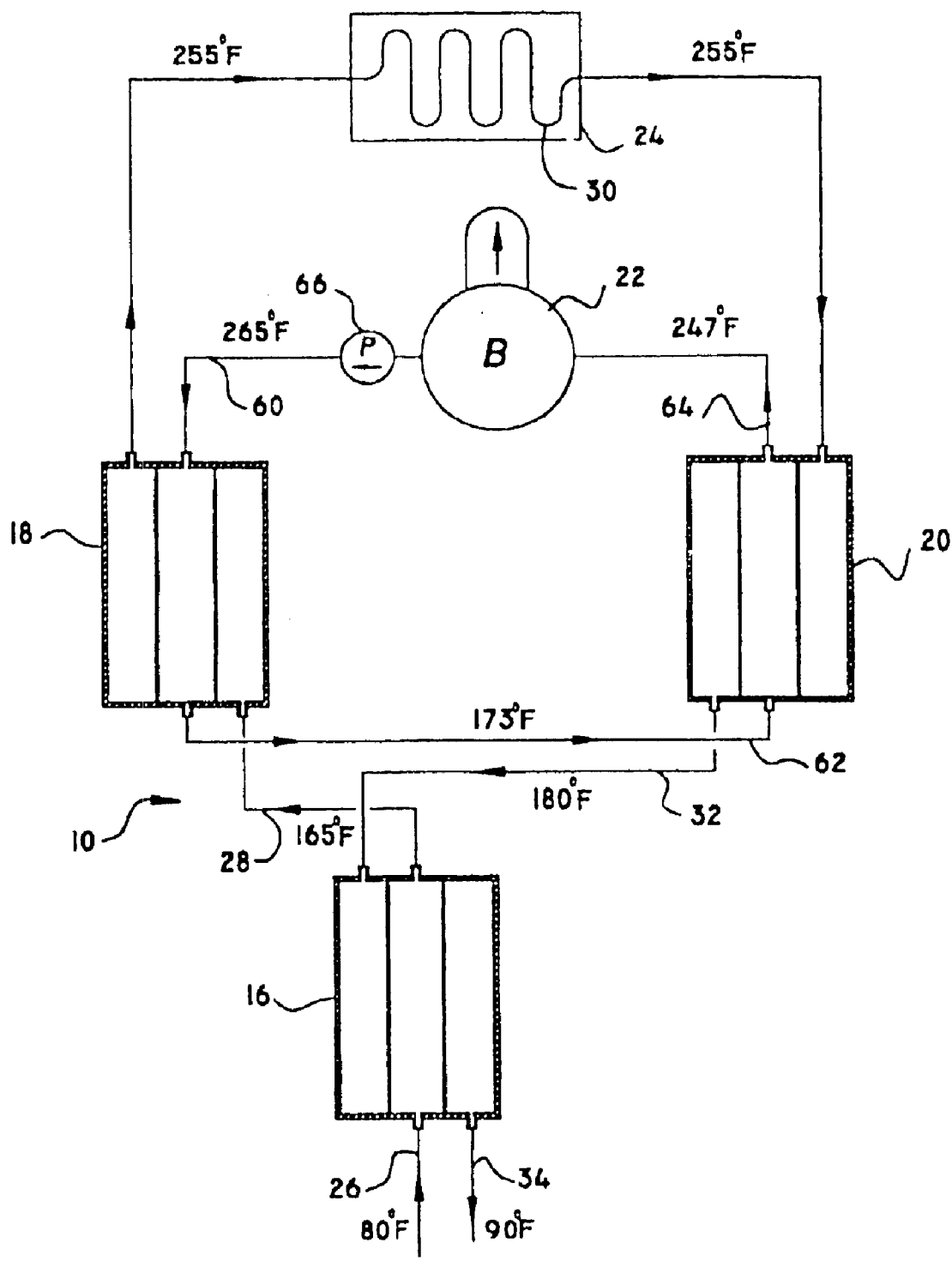
FIG. 2 is a simplified version of the schematic of FIG. 1, depicting system temperatures measured during successful operation of a sterilizing system according to this invention.

FIGS. 1 and 2 of the drawings schematically depict the major components of a system 10 for continuously sterilizing contaminatable slurry, according to a preferred embodiment of this invention. These comprise a supply tank 12, a storage tank 14, serially arranged heat exchangers 16, 18 and 20, a hot water boiler 22, and a manifold 24.

A pump 25 at supply tank 12 pumps slurry through a piping system which includes a supply pipe 26 from pump 25 to heat exchanger 16, a connecting pipe 28, that connects heat exchangers 16 and 18, slurry manifold piping 30, that connects heat exchangers 18 and 20, a connecting pipe 32, that connects heat exchangers 20 and 22, and an outlet pipe 34, that exits heat exchanger 16 and enters storage tank 14. The direction of slurry flow is indicated by arrows in FIGS. 1 and 2. Pipe 34 can, alternatively, connect directly into the intake of a further industrial process, such as paper making. Tanks 12 and 14 may be stationary, or mobile, such as mounted on a rail car, semi-trailer, or ship. Indeed, the slurry sterilizing system itself may be stationary or may be mounted on a similar mobile platform for transportation to a variety of locations for on-site processing (e.g. at an industrial plant, at dockside, or in a railroad yard).

At the initiation of the process of this invention, supply tank 12 will be filled with contaminated, or unsterilized, slurry 40, while storage tank 14 will normally be empty. This process is a continuous process, so that eventually tank 14 will fill with sterilized slurry 42. Prior to initiation of this process, at least tank 14, and pipes 34, 32, and 30, and preferably pipes 28 and 26 will be sanitized by backflushing with a sanitizing agent, such as hydrogen peroxide, supplied from a supply 44 via a delivery nozzle 46. Oxygen is purged from the system by the simultaneous introduction of nitrogen from a supply 50 via a nozzle 52.

The heating unit for the sterilizing apparatus 10 includes hot water boiler 22, and a second or hot water piping system, that includes an outlet pipe 60 from boiler 22 to heat exchanger 18, a connecting pipe 62 connecting heat exchangers 18 and 20, and an inlet pipe 64 connecting heat exchanger 20 to boiler 22. A pump 66 pumps water through the closed hot water system at a predetermined pressure in the direction indicated by arrows in the drawings. The pressure of the hot water system must be sufficient to preclude formation of steam. The heating unit and manifold 24 comprise the sterilizing unit.

A prototype/pilot sterilization system, illustrated in FIGS. 3 and 4, was constructed on a semi-trailer 70 to test and prove out the process according to this invention. This system utilized a Parker manifold comprising 60 ft. of 4" stainless steel slurry pipe and an array of 2" stainless steel hot water pipe—all enclosed in a stainless steel box containing 3" rock wool insulation. The heating system utilized a 300,000 BTU/hr. propane-fired boiler and a pumping system that pumped hot water at 30 gpm. A peristaltic slurry pump pumped slurry through the system at 17 gpm. Three substantially identical APV plate heat exchangers were interconnected by insulated piping runs of 10 ft. A 35 kW Cummins generator set powered the installation.

A target sterilizing temperature was set at about 250° F. and a holding time of about 2 minutes in the sterilizing manifold. The sterilizing temperature was actually measured at 255° F. and the time was about 2 minutes. A preferred temperature range is about 230° F.–270° F., with the time of treatment being longer than 5 seconds for a flash treatment. Treatment time is dependent on the volume of the piping used and treatment temperature. The temperature of the cooled sterilized slurry was 90° F., and a temperature below 100° F. is preferred to facilitate handling.

The system was fogged with a mist composed of a mixture of nitrogen and hydrogen peroxide emitted from tanks through a dual nozzle to sanitize the system. After the system was fired up and brought to temperature, 700 gallons of production beneficiated calcium carbonate slurry, at 75% dry solids and a density of 16 pounds/gallon volume, were pumped through the sanitized system. Temperatures in all segments of the system were monitored, as was water flow. Temperatures measured during this run are depicted in FIG. 2. Samples were taken of sterilized slurry to confirm that sterilization was complete. The test was successful, thus proving the process. It is now possible to sterilize contaminatable slurries without using bactericides or other chemicals.

This process proved to be quite economical, as the heating system recovered 90% of the boiler heat. Thus, only 10% boiler makeup is necessary. This economy results from the use of heat exchangers to transfer heat. As FIG. 2 shows, the incoming 80° F. contaminated slurry was pre-heated to 165° F. in heat exchanger 16 by the 180° F. sterilized slurry, which cooled to an exit temperature of 90° F. The preheated contaminated slurry was elevated to a sterilizing temperature in heat exchanger 18 by 265° F. hot water from boiler 22 to a temperature of 255° F., as measured in manifold 24. Hot water, which exited manifold 24 at 173° F., was reheated to 247° F. in heat exchanger 20 by sterilized slurry, which then exited at 180° F. Thus the boiler was supplied with 247° F. intake water, which it needed to elevate only 18° F.

Preferably, a mist or fog of nitrogen and hydrogen peroxide is used to sanitize the system. Sanitizing chemicals other than hydrogen peroxide may also be used to kill any bacteria in the system. As slurry from supply 40 transits slurry piping 26, 28, 30, 32 and 34 into storage tank 14, this fog is forced into storage tank 14, where the condensed hydrogen peroxide will be drained and the nitrogen will blanket slurry 42 to exclude contact with oxygen The nitrogen blanket is maintained during any subsequent shipping of tank 14 to a distant terminus by truck, rail or ship. Depending on the degree of sterilization maintained (a function of time and equipment), the transported slurry may again undergo the same sterilization process by another or similar installation of sterilizing equipment 10.

It is understood that use of the term "contaminatable slurries" herein encompasses any slurry of substances, such as kaolin, calcium carbonate, titanium dioxide, talc, latex, other carbonates, and combinations thereof which are subject to contamination by aerobic and anaerobic bacteria, and which are used as coatings, fillers, extenders and pigments in the paper, paint, rubber and plastics industries.

While only a preferred embodiment has been illustrated and described, obvious modifications are contemplated within the scope of this invention, as defined by the appended claims. For example, other types of heating systems could be used to sterilize the slurry, although systems using a liquid are preferred because of their efficiency.

I claim:

1. A process for sterilizing a contaminatable slurry to preclude aerobic and anaerobic bacteria from the slurry, comprising the steps of
   a. providing a sanitized oxygen-free fluid handling system,
   b. pumping the slurry through the system at a predetermined pressure,
   c. heating the slurry to a sterilizing temperature of about 210° F.–290° for a predetermined time to sterilize the slurry,
   d. cooling the sterilized slurry by transferring heat to the unsterilized slurry entering the process, and e. transferring the sterilized slurry to a sanitized fluid collection device.

2. The process of claim 1, including the step of flushing the fluid handling system with a mist of nitrogen and a sanitizing chemical to sanitize the system.

3. The process of claim 1, wherein the sterilizing temperature is about 230° F.–270° F. the predetermined time is greater than 5 seconds, and the cooling temperature is below 100° F.

4. The process of claim 3, wherein the sterilizing temperature is about 250° F. and the predetermined time is about 2 minutes.

5. The process of claim 1, wherein the sanitized fluid collection device is a storage tank, and including the steps of f. flushing the fluid handling system with a mist of nitrogen and a sanitizing chemical to sanitize the system, and g. excluding oxygen from the storage tank, and h. transporting the storage tank to a terminus for offloading of the slurry.

6. The process of claim 5, including the further steps of i. offloading the slurry, and j. repeating steps a–e.

7. The process of claim 1, Including the steps of f. flushing the fluid handling system with a mist of nitrogen and hydrogen peroxide to sanitize the system, g. providing a tank as the fluid collection device, and h. excluding oxygen from the tank by covering the sterilized slurry with a blanket of nitrogen.

8. The process of claim 1, wherein the fluid collection device is the supply system of a further industrial process.

9. The process of claim 1, wherein the slurry is kaolin or calcium carbonate.

10. The process of claim 1, including the step of mounting the fluid handling system on a mobile platform for transportability.

11. Fluid handling and sterilizing apparatus for sterilizing contaminatable slurries to preclude aerobic and anaerobic bacteria from the slurry, comprising a sterilizing unit for heating slurry to a sterilizing temperature, a heat exchanger for transferring heat from the sterilized slurry to the unsterilized slurry to preheat the unsterilized slurry and cool the sterilized slurry, a piping circuit connecting the pump to the heat exchanger and connecting the heat exchanger to the sterilizing unit for handling the unsterilized slurry, and connecting the sterilizing unit to the heat exchanger and exiting the heat exchanger for handling the sterilized slurry, and a pump for intaking unsterilized slurry and pumping slurry through the piping circuit at a predetermined pressure at a predetermined flow rate wherein the sterilizing unit includes a heating, unit, a second heat exchanger for transferring heat from the heating unit to the unsterilized slurry to raise the temperature of the unsterilized slurry to a sterilizing temperature, a manifold for containing the heated slurry at the sterilizing temperature, and a third heat exchanger for transferring heat from the sterilized slurry to the heating unit to cool the sterilized slurry.

12. The fluid handling and sterilizing apparatus of claim 11, wherein the manifold is sized to maintain the slurry at the sterilizing temperature for a predetermined time sufficient to fully sterilize the slurry.

13. The fluid handling and sterilizing apparatus of claim 11, wherein the heating unit comprises a hot water boiler for heating water to a second predetermined temperature, a second piping circuit interconnecting the hot water boiler, the second heat exchanger, and the third heat exchanger, and a second pump for pumping water through the second piping circuit at a second predetermined flow rate.

14. The fluid handling and sterilizing apparatus of claim 13, wherein the first predetermined flow rate is about 17 gpm, and the second predetermined flow rate is about 30 gpm.

15. The fluid handling and sterilizing apparatus of claim 11, including a source of contaminatable slurry in the form of kaolin or calcium carbonate.

16. The fluid handling and sterilizing apparatus of claim 11, where the pump is a peristaltic pump.

17. The fluid handling and sterilizing apparatus of claim 11, including a mobile platform mounting the apparatus to enable transportation to a variety of locations.

* * * * *